(12) United States Patent
Guala

(10) Patent No.: US 6,893,056 B2
(45) Date of Patent: May 17, 2005

(54) MALE LUER LOCK CONNECTOR FOR MEDICAL FLUID LINES

(75) Inventor: Gianni Guala, Turin (IT)

(73) Assignee: Industrie Borla SpA, Turin (IT)

( * ) Notice: Subject to any disclaimer, the term of this patent is extended or adjusted under 35 U.S.C. 154(b) by 112 days.

(21) Appl. No.: 10/355,168

(22) Filed: Jan. 31, 2003

(65) Prior Publication Data

US 2003/0151256 A1 Aug. 14, 2003

(30) Foreign Application Priority Data

Feb. 8, 2002 (IT) ...................................... TO2002A0111

(51) Int. Cl.[7] .......................... F16L 25/00; A61M 25/18; A61M 39/10
(52) U.S. Cl. ...................... 285/332.1; 285/332; 285/92; 604/533; 604/534; 604/535
(58) Field of Search ........................ 285/92, 332, 332.1, 285/354; 604/533, 534, 535

(56) References Cited

U.S. PATENT DOCUMENTS

| | | | | |
|---|---|---|---|---|
| 3,055,363 A | * | 9/1962 | Eckhart ...................... 604/242 |
| 3,459,177 A | * | 8/1969 | Deuschle ...................... 600/579 |
| 4,735,441 A | * | 4/1988 | Stephens ................ 285/148.19 |
| 5,047,021 A | * | 9/1991 | Utterberg ...................... 604/533 |
| 5,507,733 A | * | 4/1996 | Larkin et al. ................ 604/534 |
| 5,620,427 A | * | 4/1997 | Werschmidt et al. ........ 604/535 |
| 5,651,776 A | * | 7/1997 | Appling et al. .............. 604/534 |
| 5,702,374 A | * | 12/1997 | Johnson ....................... 604/533 |
| 5,782,505 A | * | 7/1998 | Brooks et al. .......... 285/148.19 |
| 5,984,373 A | * | 11/1999 | Fitoussi et al. ................ 285/92 |
| 6,260,890 B1 | * | 7/2001 | Mason ......................... 285/332 |
| 6,332,633 B1 | * | 12/2001 | Fitoussi et al. .............. 285/332 |

* cited by examiner

Primary Examiner—James M. Hewitt
(74) Attorney, Agent, or Firm—Sughrue Mion, PLLC

(57) ABSTRACT

A male luer lock connector for medical fluid lines comprising an elongated tubular body having an end portion with external luer cone and an internally threaded bushing mounted so that it can turn and slide on a portion with a cylindrical external surface of the tubular body. The axial backward travel of the bushing allows axial engagement of the male connector with a female luer lock connector even without screwing the bushing, and it is provided with a cam front reaction surface with which the bushing interacts to voluntarily produce axial expulsion of the female luer lock connector.

7 Claims, 4 Drawing Sheets

MALE LUER LOCK CONNECTOR FOR MEDICAL FLUID LINES

BACKGROUND OF THE INVENTION

The present invention relates in general to connectors for medical fluid lines, and more specifically regards a male luer lock connector of the type comprising an elongated tubular body having a portion with a cylindrical external surface and an end portion with an external luer cone, and a bushing having an internal thread in which a female luer lock connector can be screwed, the end portion with external luer lock of the tubular body of the male luer lock connector being designed to engage axially with the female luer lock connector.

STATE OF THE PRIOR ART

Traditionally, the bushing is fixed in relation to the tubular body of the connector, since it is integral with the portion with the cylindrical external surface of said tubular body. More recently, solutions have been proposed in which the bushing is mounted on the portion with cylindrical external surface of the tubular body in such a way that it can turn and slide for an axial advance travel of a definite length starting from a drawn-back position.

This embodiment has the advantage that the male luer lock connector can be connected and fastened to the female luer lock and can be released and detached from the latter without it being necessary to rotate the tubular body, and hence without any deformation and twisting of the flexible tube of the medical line attached, on one side, to the male connector and, on the other, to the female connector.

These solutions with bushing that turns and slides are substantially of two types.

In a first type the axial travel of the bushing has a length that consents firm engagement of the end portion with external luer cone of the body of the male connector inside the female connector without having to screw the internal thread of the bushing even partially on the female luer lock connector. This arrangement is relatively safe from the viewpoint of use, as the connection between the male connector and the female connector is to a certain extent guaranteed even following simple axial engagement between the respective luer cones, that is even if the bushing of the male connector is not screwed fully down on the female connector due to inattentiveness or inexperience of the operator. On the other hand, this arrangement has the drawback that disengagement and voluntary separation between the male connector and the female connector requires, after unscrewing the bushing, a certain degree of manual force for reciprocal axial removal of the respective luer cones. This operation may hence be difficult and awkward.

In a second type of known connector of the type specified above the axial travel of the bushing along the portion with cylindrical external surface of the tubular body of the male connector is reduced so as to prevent firm engagement of the end portion with external luer cone of the male connector in the female luer lock connector without at least partially screwing the internal thread of the bushing on the female connector. This derives from the fact that in this arrangement the portion with cylindrical external surface has an annular frontal reaction part which the bushing is designed to axially contrast in its drawn-back position to produce during use, after unscrewing the bushing in relation to the female luer lock connector, axial expulsion of said female luer lock connector from said end portion with external luer cone of the tubular body of the male connector. In practice this produces an effect of self-separation between the male connector and the female connector when the bushing is further unscrewed to its drawn-back position, hence facilitating the operation to separate the male connector in relation to the female connector. This advantage is nonetheless offset by the drawback that unskilled, inattentive or negligent operators may make the connection between the male connector and the female connector without screwing the bushing fully down, and therefore in a slack and unstable manner, with the danger of accidental separation between the two connectors and serious consequences for the patient to which the medical line is applied.

SUMMARY OF THE INVENTION

The object of the present invention is to attain the advantages of the two known solutions described above, while eliminating the relative drawbacks.

According to the invention this object is attained thanks to a male luer lock connector of the type stated in the pre-characterizing part of claim 1, characterized by the following combination of characteristics:

said axial travel of the bushing has a length that allows, in said drawn-back position of said bushing, substantially firmly engagement of said end portion with external luer cone of the body of the male connector with said female luer lock connector without even partially screwing said internal thread of said bushing on said female luer lock connector, said annular reaction part is formed of a cam surface that allows the bushing in said drawn-back position to be positioned in at least a partially advanced condition to produce during use said axial expulsion of said female luer lock connector.

Thanks to this idea of solution the male luer lock connector according to the invention is capable of guaranteeing during use a degree of safety equivalent to the aforesaid known connectors of the first type, together with the same ease of voluntary separation from the female connector typical of the aforesaid known connectors of the second type.

BRIEF DESCRIPTION OF THE DRAWINGS

The invention shall now be described in detail with reference to the accompanying drawings, provided purely as a non-limiting example, in which.

DETAILED DESCRIPTION OF THE INVENTION

Figure 1:
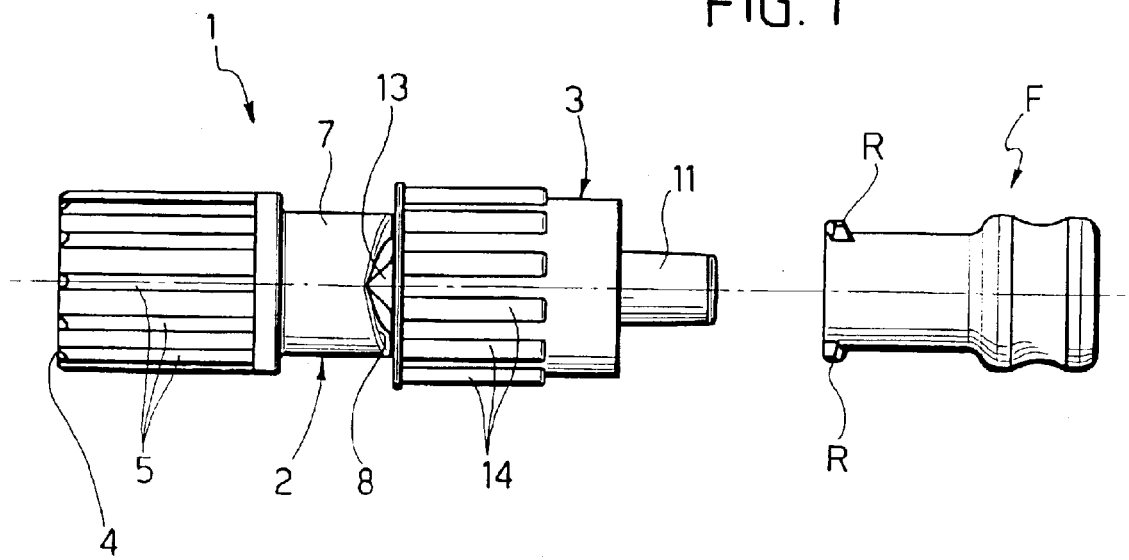
FIG. 1 is a side elevation of a schematic view of a male luer lock connector according to the invention represented in a condition prior to connection to a female luer lock connector.
Figure 2:
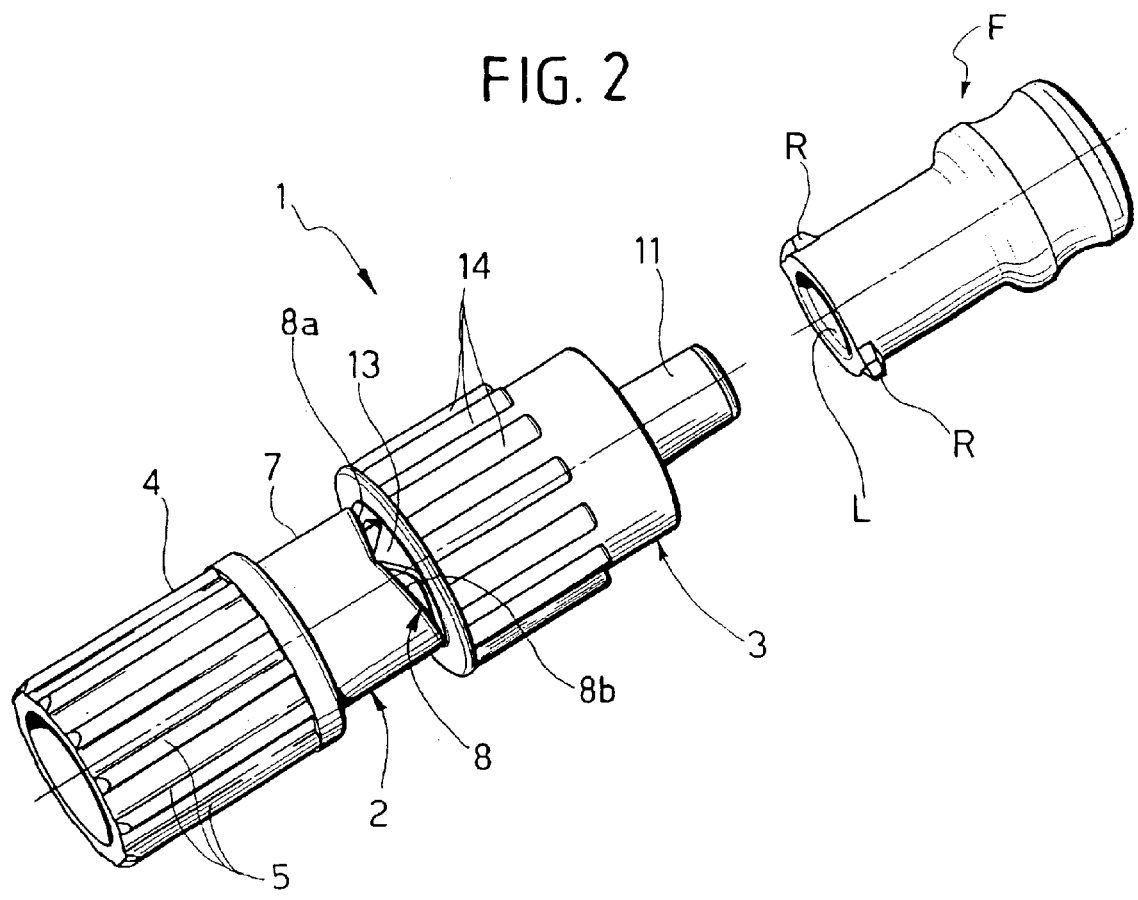
FIG. 2 is a perspective view of FIG. 1 on a larger scale.

Firstly with reference to FIGS. 1 and 2, the numeral 1 indicates generically a male luer lock connector according to the invention for medical fluid lines, for example for haemodialysis.

The male luer lock connector 1 is formed of two components, both of moulded plastic material: an elongated tubular body 2 and an internally threaded bushing 3.

Figure 4:
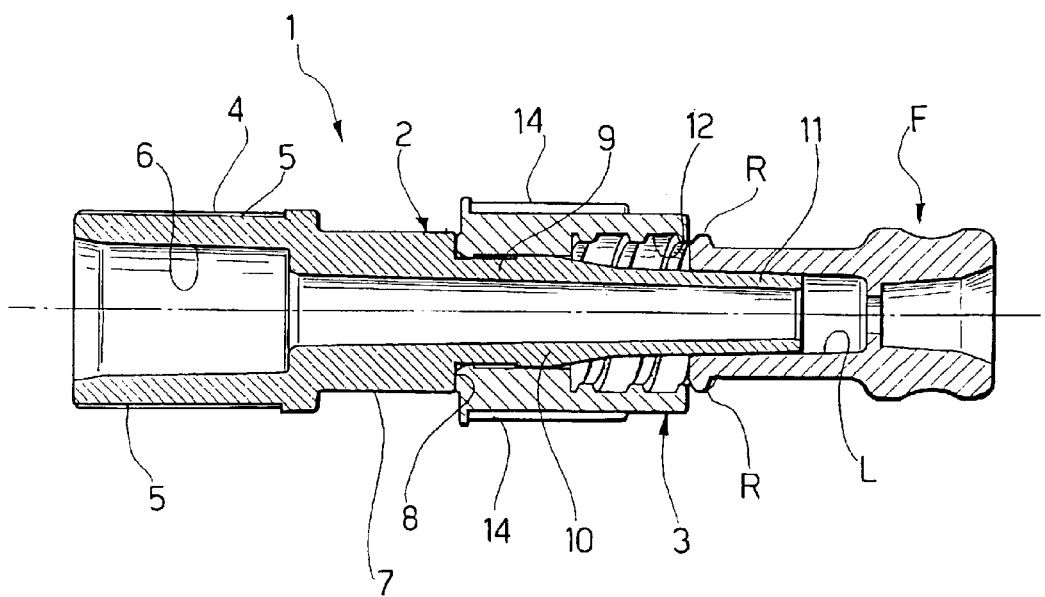
FIG. 4 is a longitudinal sectional view of FIG. 3.
Figure 7:
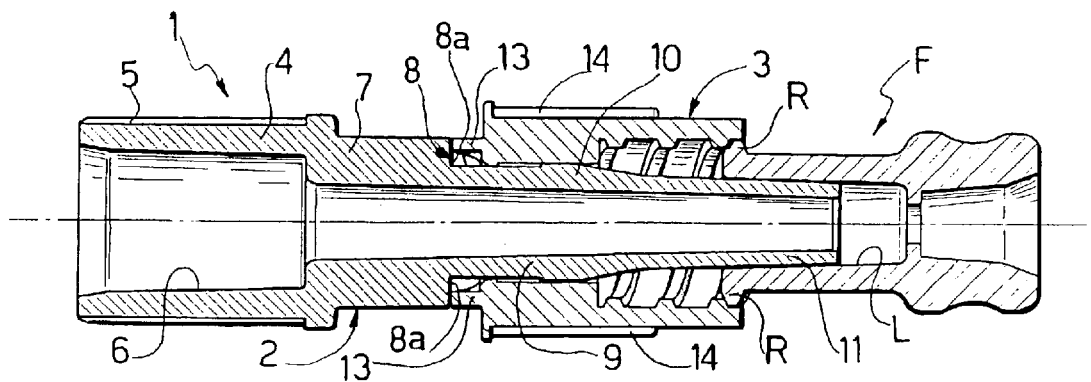
FIG. 7 is a longitudinal sectional view of FIG. 6.

The elongated tubular body 2 includes, in a single piece, an initial maneuvering part 4 provided with longitudinal gripping projections 5 and the cavity of which, indicated with 6 in FIGS. 4 and 7, is predisposed for connection of the end of a flexible tube not shown in the drawings. The maneuvering part 4 is followed by a cylindrical intermediate part 7 in turn joined, through an annular frontal reaction part indicated generically with 8, to a portion with a cylindrical surface 9 of smaller diameter, visible in FIGS. 4, 5 and 7. The portion with cylindrical external surface 9 connects, through a slightly widened portion 10, to an end portion with external luer cone 11.

The cylindrical intermediate part 7 can be omitted, and in this case the annular frontal reaction part 8 will coincide with the edge of the maneuvering part 4 facing the end portion with external luer cone 11.

The bushing 3 has an internal thread 12 (FIGS. 4, 5 and 7) and, externally, a series of axial maneuvering projections 14. This bushing 3 is mounted on the portion with cylindrical external surface 9 of the tubular body 2 in such a way that it can both turn and axially slide for a travel of axial advance of a definite length starting from a drawn-back position, shown in FIGS. 1, 2, 3 and 4. This drawn-back position is defined by the axial arrest between the bushing 3 and the annular frontal reaction part 8 of the tubular body 2. The extent of axial advance of the bushing 3 corresponds to the length of the portion with cylindrical external surface 9 between the annular frontal reaction part 8 and the widened portion 10.

According to a first fundamental characteristic of the invention, this annular part of reaction is formed of a cam surface with generally helical rising/falling travel and at least in part complementary to the surface of the internal thread 12 of the bushing 3. More specifically, the cam surface 8 comprises, in the case of the illustrated example, a pair of rising ramps 8a separated by a pair of falling ramps 8b, which may all have equal angular width. According to a variant not shown the travel of the rising ramps 8a may be steeper than that of the falling ramps 8b.

The difference in level between the highest parts and the lowest parts defined by the ramps 8a, 8b may for example be equal to or greater than the pitch of the internal thread 12 of the bushing 3.

To cooperate in the clarified manner subsequently with the cam profile 8, in the case of the example shown, the bushing 3 has a pair of diametrally opposite cam-follower projections 13 at its back end.

According to a second fundamental characteristic of the invention, the extent of axial travel of the bushing 3 along the cylindrical surface 9 of the body 2 towards the fully drawn-back position shown in FIGS. 1, 2 3 and 4, in which the cam-followers 13 are positioned at the lowest parts defined between each pair of rising 8a and falling 8b ramps, is as has been said closely connected to the manner of engagement of the male luer lock connector 1 with the complementary female luer lock connector, indicated as a whole with F in the drawings. This female luer lock connector F comprises, in the usual manner, a tubular body of moulded plastic material predisposed for example (although not necessarily) for the connection of a flexible tube, and an internal luer cone L, complementary to the end portion with external luer cone 11 of the male luer lock connector 1. The internal luer cone L is formed at its free end with external radial projections R which can engage with the thread 12 of the bushing 3. The projections R may be replaced by an external thread.

The extent of the axial travel of the bushing 3 along the portion with cylindrical external surface 9 between the fully advanced position (shown in FIG. 5) and the fully drawn-back position in FIGS. 1, 2, 3 and 4, in which as has been said the cam-followers 13 are positioned at the lowest parts of the cam profile 8, is determined in such a way as to allow, in the fully drawn-back position of the bushing 3, substantially firm engagement (with interference) of the end portion with external luer cone 11 of the body 2 of the male connector 1 inside the internal luer cone L of the female luer lock connector F without it being necessary to even partially screw the internal thread 12 of the bushing 3 on the projections R of the female luer lock connector F. Conversely, this effect is not possible in the partially drawn-back position of the bushing 3 in which the cam-followers 13 are positioned at the highest parts of the cam profile 8.

Operation of the male luer lock connector 1 described is as follows.

FIGS. 1 and 2 show the condition prior to the phase to introduce the male connector 1 in the female connector F: in this condition the bushing 3 is disposed in its fully drawn-back position, with the cam followers 13 positioned angularly and axially at the lowest parts of the cam profile 8. In this position the end portion with external luer cone 11 projects beyond the bushing 3 for a length which, as has been said, allows it to engage with interference inside the internal luer cone L of the female connector F without requiring to even partially screw the internal thread 12 of the bushing 3 on the projections R. This condition of reciprocal axial engagement at least in part forced is represented in FIGS. 3 and 4: as can be seen, with the bushing 3 in the fully drawn-back position and with the projections R disposed at the front end of said bushing 3 the external luer cone 11 of the male connector 1 is engaged axially with interference inside the internal luer cone L of the female connector F: the union between the two connectors is thus to some extent guaranteed even if an unskilled or negligent operator does not screw the bushing fully down on the projections R.

Figure 3:
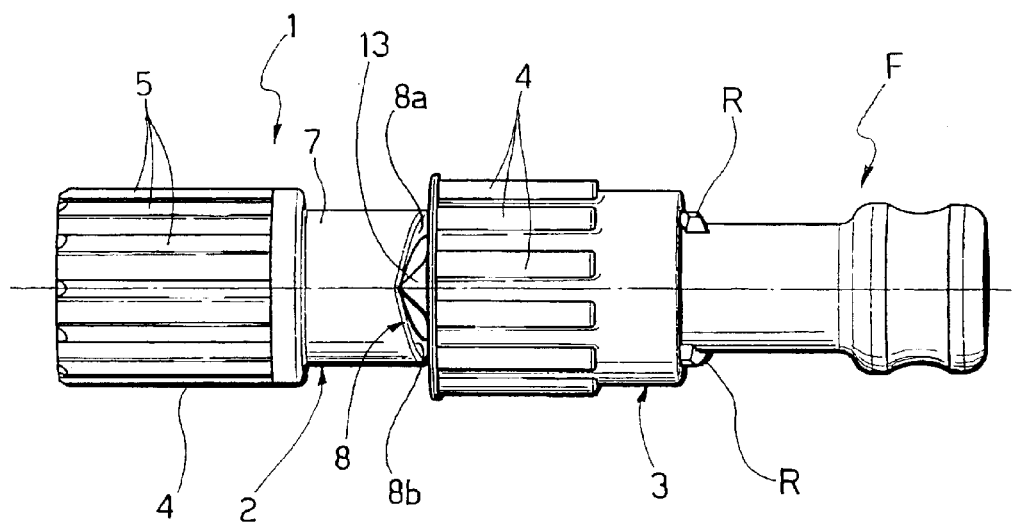
FIG. 3 is an analogous view to FIG. 1 on a larger scale of the male connector represented in the initial phase of connection to the female connector.
Figure 5:
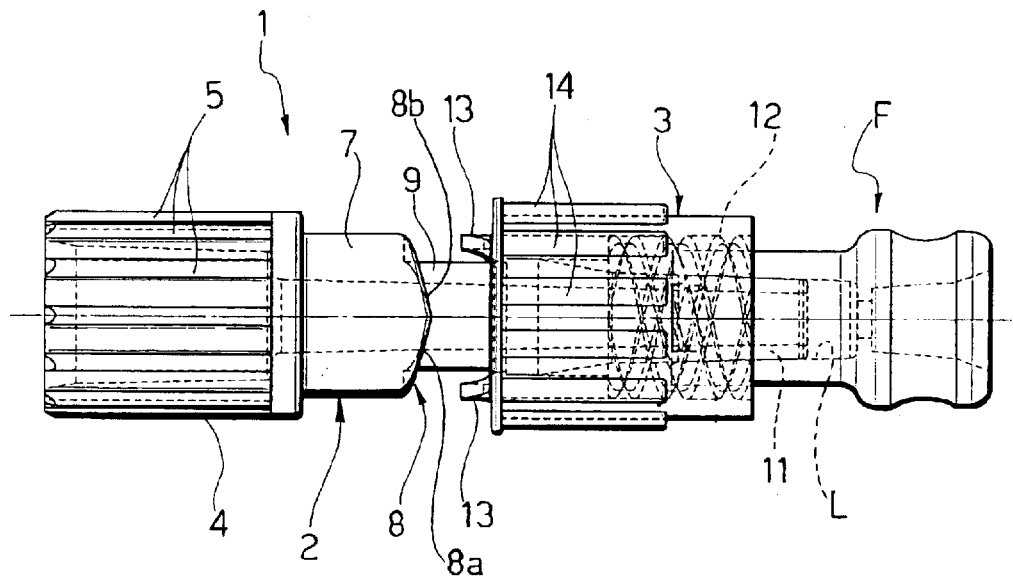
FIG. 5 is an analogous view to FIG. 3 showing the male connector engaged with and fastened to the female connector.
Figure 6:
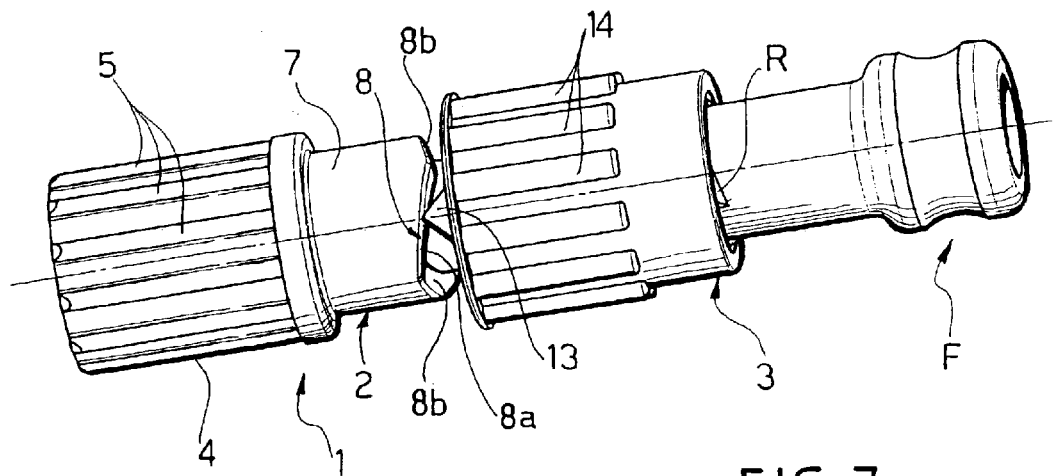
FIG. 6 is a perspective view showing the phase of separation between the male connector and the female connector.

Starting from the condition in FIGS. 3 and 4, screwing of the internal thread 12 of the bushing 3 on the projections R of the female connector F produces further axial force of the external luer cone 10 in the internal luer cone L, when the bushing 3, through the effect of being screwed, reaches the fully advanced position on the portion with cylindrical external surface 9, as shown in FIG. 5. In this position engagement of the male luer lock connector 1 in relation to the female luer lock connector L is stably and securely fastened, guaranteeing the maximum degree of safety against risks of accidental disconnection caused by any movements, knocks, thermal dilation, etc.

To produce voluntary disconnection between the two connectors 1 and F it is necessary to unscrew the bushing 3 until it reaches the fully drawn-back position with the cam-follower projections 13 inserted at the lowest parts of the cam profile 8. Starting from this position, further unscrewing rotation of the bushing 3 causes the cam-follower projections 13 to move up the rising ramps 8a of the cam profile 8: this produces a frontal axial reaction of the bushing 3 which, thanks to interaction between the end part of the internal thread 12 and the projections R, acts as an extractor producing axial thrust against the female connector F towards the outside of the male connector 1, the effect of which causes the external luer cone 11 of the latter to disengage from the internal luer cone L, with an action of axial expulsion.

It appears evident from the above that the male luer lock connector according to the invention is able to guarantee, compared with known connectors of the same type, on the one hand greater safety against risks of accidental disconnection from the female connector if reciprocal connection is performed in a slack or incorrect manner, and on the other hand a more practical and easier action of voluntary disconnection of the male connector in relation to the female connector, with minimum manual force. The latter effect may be further increased if, as already mentioned above, the travel of the rising ramps 8a of the cam profile 8 is steeper than that of the falling ramps 8b.

Figure 8:
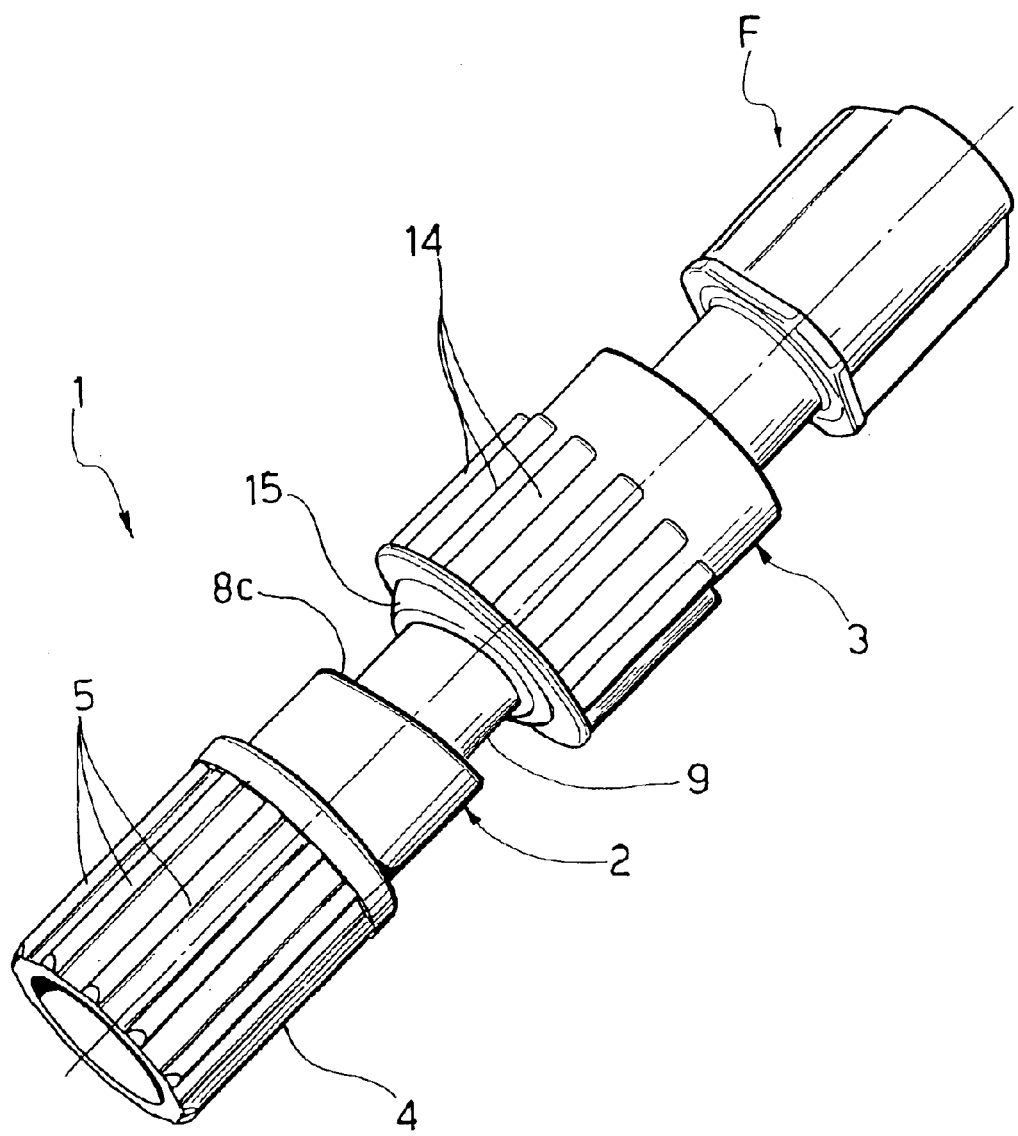
FIG. 8 is an analogous view to FIG. 5 showing a variant of the male luer lock according to the invention.

Naturally, the constructional details and embodiments may vary widely from those described and illustrated, without however departing from the scope of the present invention as defined in the claims below. Therefore, for example, the cam profile 8 may have a different configuration to the one describe with reference to the drawings, and consist, for example, of a single pair of rising and falling ramps 8a, 8b; in this case the cam profile 8 could have an angular width of even a mere 180°, and the bushing 3 would be provided with a single cam-follower projection 13. Alternatively, and as shown in the variant in FIG. 8 in which parts identical or similar to those described above are indicated with the same numerical references, the cam profile 8 could consist of a simple beveled inclined flat surface 8c and the cam-follower function could be produced by a complementary inclined surface 15 of the back end of the bushing 3.

What is claimed is:

1. A male luer lock connector for medical fluid lines comprising an elongated tubular body having a portion with a cylindrical external surface and an end portion with an external luer cone, and a bushing mounted or said cylindrical external surface of said tubular body so that it can turn and slide for an axial advance travel of a definite length starting from a drawn-back position, said bushing having an internal thread in which a female luer lock connector can be screwed, said end portion with said external luer cone of said tubular body being designed to engage axially with said female luer lock connector, in which said portion with said cylindrical external surface has an annular front reaction part which said bushing is designed to axially contrast, in said drawn-back position, to produce during use, after unscrewing said bushing relative to said female luer lock connector, axial expulsion of said female luer lock connector from said end portion with said external luer cone of said tubular body, wherein:

said axial travel of said bushing has a length that allows, in said drawn-back position of said bushing, substantially firm engagement of said end portion with said external luer cone of said body of said male connector with said female connector without even partially screwing said internal thread of said bushing on said female luer lock connector, said annular front reaction part is formed of a cam surface to allow said bushing in said drawn-back position to be positioned in at least a partially advanced condition to produce during use said axial expulsion of said female luer lock connector, and wherein said cam surface has generally helical profiles at least in part complementary to said internal thread.

2. Connector according to claim 1, wherein said helical profiles include at least a pair of rising/falling ramps.

3. Connector according to claim 2, wherein said helical profiles include two pairs of alternate rising/falling ramps.

4. Connector according to claim 2, wherein said rising ramps are steeper than said falling ramps.

5. Connector according to claim 1, wherein said cam surface is a flat inclined surface.

6. Connector according to claim 1, wherein said bushing has cam-follower formations cooperating with said cam surface.

7. Luer lock connection assembly for medical fluid lines comprising a female luer lock connector and a male luer lock connector according to claim 1.

* * * * *